US011638431B2

(12) United States Patent
Kawanabe et al.

(10) Patent No.: US 11,638,431 B2
(45) Date of Patent: May 2, 2023

(54) FERMENTED MILK AND POLYSACCHARIDE WITH CANCEROUS CACHEXIA INHIBITORY EFFECT

(71) Applicant: MEIJI CO., LTD., Tokyo (JP)

(72) Inventors: Hirotaka Kawanabe, Kanagawa (JP); Marie Nakamura, Kanagawa (JP)

(73) Assignee: MEIJI CO., LTD., Tokyo (JP)

( * ) Notice: Subject to any disclaimer, the term of this patent is extended or adjusted under 35 U.S.C. 154(b) by 324 days.

(21) Appl. No.: 16/650,184

(22) PCT Filed: Oct. 29, 2018

(86) PCT No.: PCT/JP2018/040016
§ 371 (c)(1),
(2) Date: Mar. 24, 2020

(87) PCT Pub. No.: WO2019/087993
PCT Pub. Date: May 9, 2019

(65) Prior Publication Data
US 2020/0296979 A1    Sep. 24, 2020

(30) Foreign Application Priority Data

Oct. 31, 2017 (JP) .............................. JP2017-210401

(51) Int. Cl.
| A61K 35/747 | (2015.01) |
| C08B 37/00 | (2006.01) |
| A23C 9/123 | (2006.01) |
| A23L 33/125 | (2016.01) |
| A23L 33/135 | (2016.01) |
| A61P 35/00 | (2006.01) |

(52) U.S. Cl.
CPC ............ A23C 9/123 (2013.01); A23L 33/125 (2016.08); A23L 33/135 (2016.08); A61K 35/747 (2013.01); A61P 35/00 (2018.01)

(58) Field of Classification Search
CPC ..... A23C 9/123; A23C 9/1234; A23L 33/135; A61K 35/747; A61K 35/20; A23V 2002/00; A23Y 2220/29; C08B 37/00
See application file for complete search history.

(56) References Cited

U.S. PATENT DOCUMENTS

| 6,261,560 | B1 | 7/2001 | Tsujinaka et al. | |
| 7,901,925 | B2* | 3/2011 | Bojrab ................. | A61K 35/747 |
| | | | | 435/252.9 |
| 2010/0041746 | A1 | 2/2010 | D'Orazio et al. | |
| 2010/0310513 | A1 | 12/2010 | Daube et al. | |
| 2012/0064051 | A1 | 3/2012 | Mercenier et al. | |
| 2012/0107287 | A1 | 5/2012 | Mercenier et al. | |
| 2012/0114701 | A1 | 5/2012 | Petit et al. | |
| 2012/0121561 | A1 | 5/2012 | Mercenier et al. | |
| 2012/0121563 | A1 | 5/2012 | Mercenier et al. | |
| 2012/0121652 | A1 | 5/2012 | Mercenier et al. | |
| 2012/0121685 | A1 | 5/2012 | Mercenier et al. | |
| 2012/0128726 | A1 | 5/2012 | Mercenier et al. | |
| 2012/0135044 | A1 | 5/2012 | Mercenier et al. | |
| 2012/0141444 | A1 | 6/2012 | Mercenier et al. | |
| 2012/0183514 | A1 | 7/2012 | Mercenier et al. | |
| 2012/0183515 | A1 | 7/2012 | Mercenier et al. | |
| 2012/0189598 | A1 | 7/2012 | Mercenier et al. | |
| 2012/0195867 | A1 | 8/2012 | Mercenier et al. | |
| 2012/0269789 | A1 | 10/2012 | Mercenier et al. | |
| 2013/0028877 | A1 | 1/2013 | Petit et al. | |
| 2013/0039889 | A1 | 2/2013 | McDonagh et al. | |
| 2013/0023660 | A1 | 9/2013 | Peneva et al. | |
| 2013/0236600 | A1* | 9/2013 | Peneva ................. | C12N 1/205 |
| | | | | 435/252.9 |
| 2013/0260440 | A1 | 10/2013 | Petit et al. | |
| 2015/0079056 | A1 | 3/2015 | Mercenier et al. | |
| 2016/0206733 | A1* | 7/2016 | Makino ................ | A61K 35/747 |
| 2016/0339064 | A1 | 11/2016 | Kovarik et al. | |
| 2020/0296979 | A1 | 9/2020 | Kawanabe et al. | |

FOREIGN PATENT DOCUMENTS

| CN | 104905246 | 9/2015 |
| JP | 2009-537582 | 10/2009 |
| JP | 2011-501666 | 1/2011 |
| JP | 2011-139700 | 7/2011 |
| JP | 2012-526757 | 11/2012 |
| JP | 2013-511261 | 4/2013 |

(Continued)

OTHER PUBLICATIONS

Dev et al. The Evolving Approach to Management of Cancer Cachexia. Oncology (Williston Park). 2017;31(1):23-32.*
International Search Report dated Jan. 22, 2019 in International (PCT) Application No. PCT/JP2018/040016.
Kano et al., "Oral administration of milk fermented with *Lactobacillus delbrueckii* ssp. *bulgaricus* OLL1073R-1 to DBA/1 mice inhibits secretion of proinflammatory cytokines" Cytotechnology, 2002, vol. 40, No. 1-3, pp. 67-73.
Ando et al., "Tocilizumab, a Proposed Therapy for the Cachexia of Interleukin6-Expressing Lung Cancer", PLoS One, 2014, vol. 9, No. 7, e102436, pp. 1-10.
Zaki et al., "CNTO 328, a Monoclonal Antibody To IL-6, Inhibits Human Tumor-Induced Cachexia in Nude Mice", International Journal of Cancer, 2004, vol. III, No. 4, pp. 592-595.

(Continued)

*Primary Examiner* — Lynn Y Fan
(74) *Attorney, Agent, or Firm* — Wenderoth, Lind & Ponack, L.L.P.

(57) ABSTRACT

An object of the present invention is to provide a fermented milk and polysaccharide capable of inhibiting cancerous cachexia. A fermented milk with cancerous cachexia inhibitory effect according to one aspect of the present invention contains *Lactobacillus delbrueckii* subsp. *bulgaricus* as an active ingredient. Also, polysaccharide with cancerous cachexia inhibitory effect according to another aspect of the present invention are produced from the *Lactobacillus delbrueckii* subsp. *bulgaricus*. It is preferable that the *Lactobacillus delbrueckii* subsp. *bulgaricus* is *Lactobacillus delbrueckii* subsp. *bulgaricus* OLL1073R-1 (accession number: FERM BP-10741).

4 Claims, 2 Drawing Sheets

(56) References Cited

FOREIGN PATENT DOCUMENTS

| JP | 2014-27925 | 2/2014 |
|---|---|---|
| WO | 96/25174 | 8/1996 |
| WO | 2007/140613 | 12/2007 |
| WO | 2017/135364 | 8/2017 |
| WO | 2018/194149 | 10/2018 |
| WO | 2019/087993 | 5/2019 |

OTHER PUBLICATIONS

Uenishi et al., "Physiological functions and the factors of lactic acid bacterium" 2013, vol. 46, No. 2, pp. 129-133, with English Abstract.

Moro-García, Marco Antonio et al., "Oral supplementation with *Lactobacillus delbrueckii* subsp. *bulgaricus* 8481 enhances systemic immunity in elderly subjects", American Aging Association, 2013, vol. 35, pp. 1311-1326.

Chapman, Therese M. et al., "VSL#3 Probiotic Mixture", Drugs, 2006, vol. 66, pp. 1371-1387.

Sakamoto, Masahiro et al., "Usefulness of clarithromycin treatment for patients with unresectable non-small cell lung cancer", Japanese Journal of Chemotherapy, 1998, vol. 46, No. 2, pp. 87-89, with English abstract.

Sakamoto, Masahiro et al., "Long-term clarithromycin treatment for cancer cachexia of inoperable non-small cell lung cancer patients", Japanese Journal of Chemotherapy, 1996, vol. 44, No. 12, pp. 879-882, with English absuact.

Amitani, Haruka et al., "Mechanism and Nutrition in Cachexia", Japanese Society of Psychosomatic Medicine, 2016, vol. 56, No. 10, pp. 1013-1022, with English abstract.

Dongchang et al., "Clinical effect of microecological preparation on digestive tract complications and nutritional status after esophageal cancer surgery", Chinese Journal of Clinical Thoracic and Cardiovascular Surgery, Mar. 2020, vol. 27, No. 3, pp. 312-317, with English Abstract.

* cited by examiner

[Figure 1]
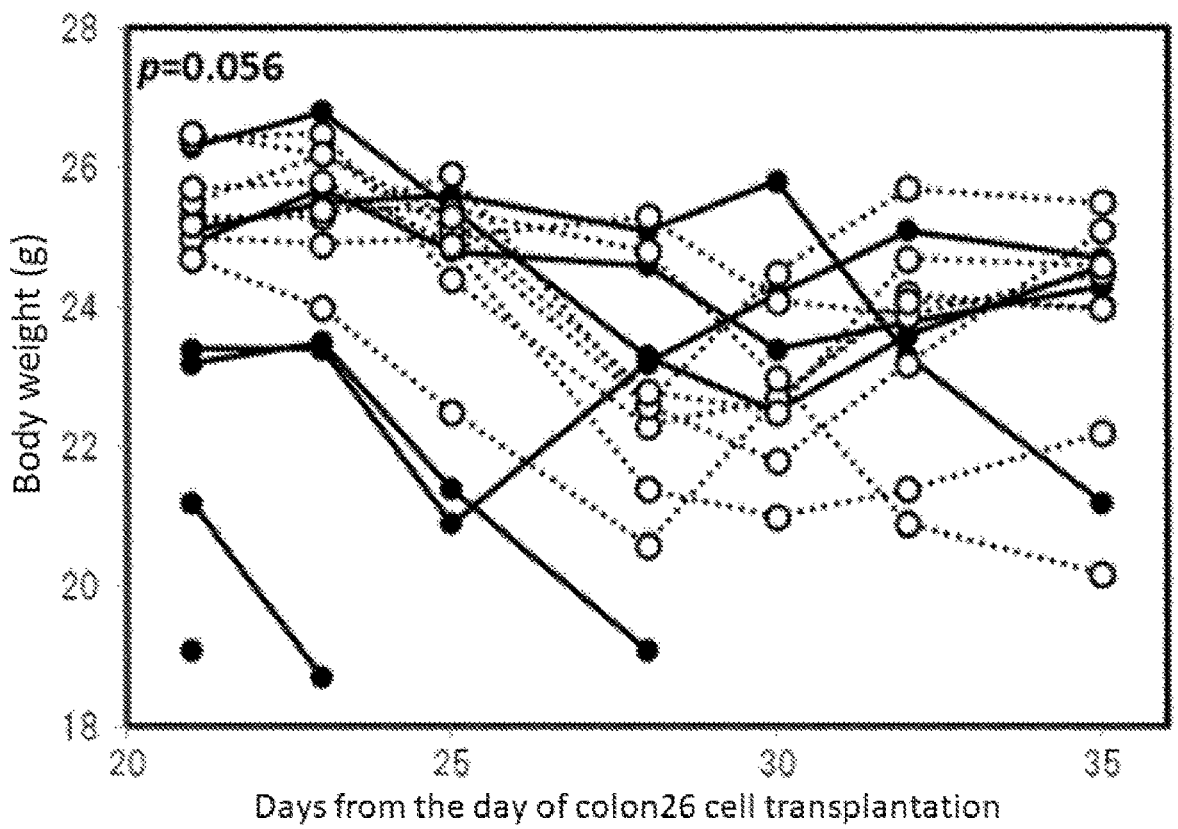
[Figure 2]
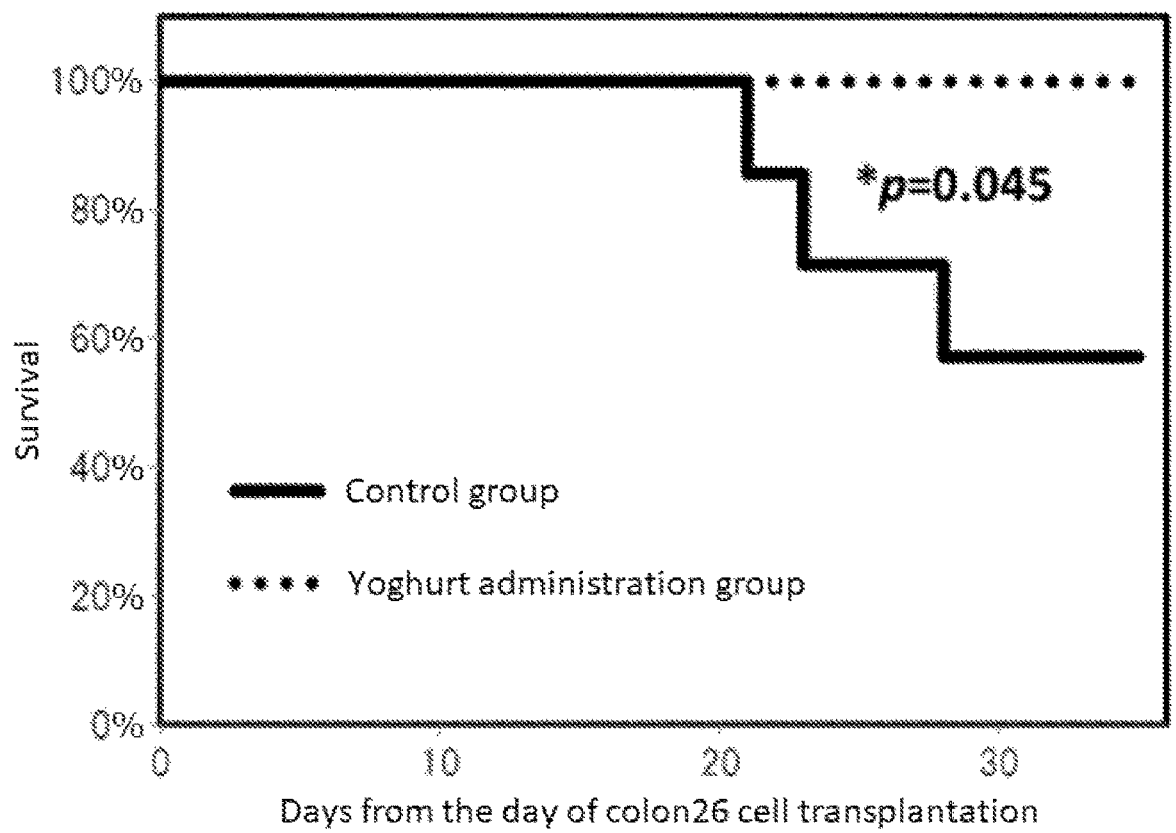

[Figure 3]
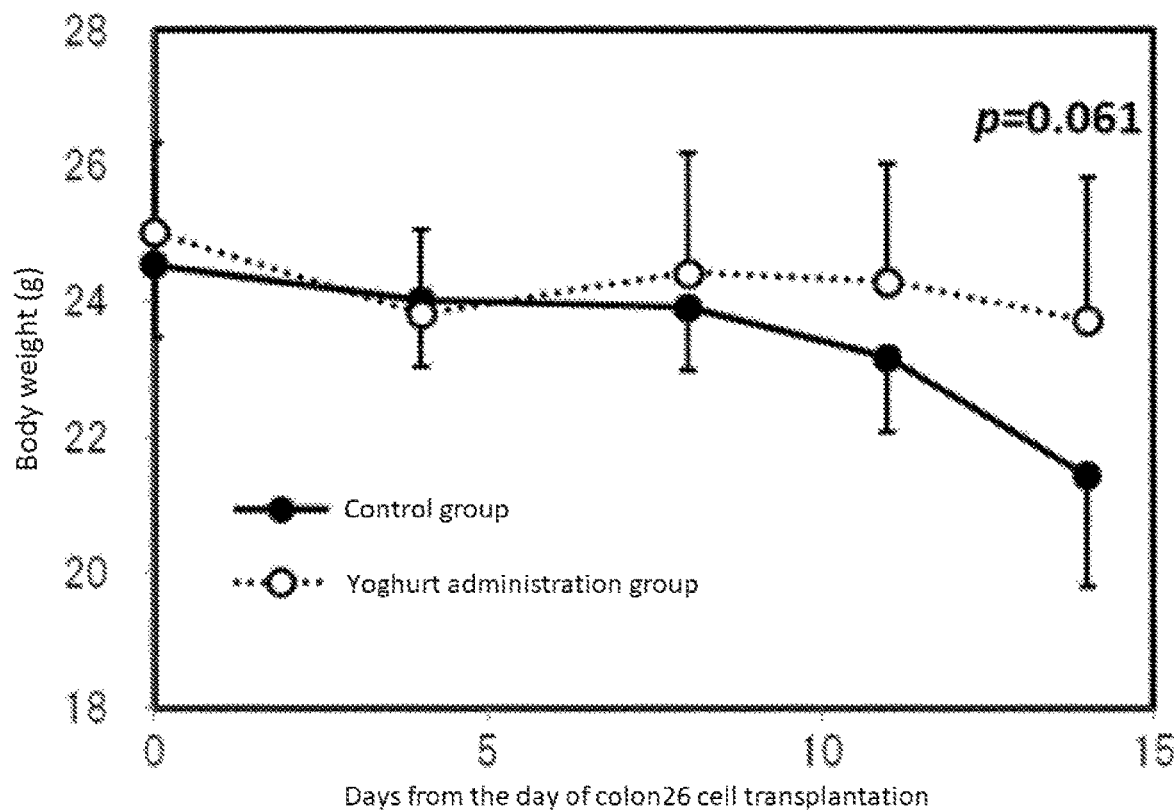

FERMENTED MILK AND POLYSACCHARIDE WITH CANCEROUS CACHEXIA INHIBITORY EFFECT

TECHNICAL FIELD

The present invention relates to a fermented milk (yoghurt) having an inhibitory effect on cancerous cachexia. The present invention also relates to a polysaccharide having an inhibitory effect on cancerous cachexia.

BACKGROUND OF THE INVENTION

In the past, genetically modified lactic acid probiotics, *Bifidobacterium*, organic compounds and the like having an inhabitation and treatment effect against cachexia were reported (see, for example, Japanese Patent Application Laid-Open No. 2013-511261, No. 2011-501666, and No. 2009-537582).

PRIOR ART LITERATURE

Patent Document

[Patent Document 1] Japanese Patent Application Laid-Open No. 2013-511261
[Patent Document 2] Japanese Patent Application Laid-Open No. 2011-501666
[Patent Document 3] Japanese Patent Application Laid-Open No. 2009-537582

SUMMARY OF THE INVENTION

Problem to be Solved by the Invention

However, it is not clear whether the above-mentioned substances work against cancerous cachexia (here, "cancerous cachexia" is a complex metabolic disorder characterized by a loss of skeletal muscle that occurs in a patient with advanced cancer. A patient with cancerous cachexia is debilitated by weight loss and loss of appetite that sometimes as a direct cause of death).

An object of the present invention is to provide a fermented milk and polysaccharide capable of inhibiting cancerous cachexia.

Means for Solving the Problems

A fermented milk with cancerous cachexia inhibitory effect according to one aspect of the present invention contains *Lactobacillus delbrueckii* subsp. *bulgaricus* as an active ingredient. It is preferable that the *Lactobacillus delbrueckii* subsp. *bulgaricus* be *Lactobacillus delbrueckii* subsp. *bulgaricus* OLL1073R-1 (accession number: FERM BP-10741).

Incidentally, when the above-mentioned fermented milk was orally administered to cancerous cachexia model mice, the survival of model mice was improved, and the progression of weight loss was suppressed, and the serum concentrations of inflammatory cytokines (IL-1β, TNF-α) and the serum concentrations of inflammation-related chemokines (CXCL1) were decreased. That is, the above-mentioned "a fermented milk with cancerous cachexia inhibitory effect" can also be expressed as "a fermented milk with improving effect of survival of a patient with cancerous cachexia", "a fermented milk with suppressing effect of weight loss of a patient with cancerous cachexia", "a fermented milk with lowering effect of serum concentration of inflammatory cytokines", "a fermented milk with lowering effect of serum concentration of inflammation-related chemokines", "a fermented milk with suppressing effect of excessive serum concentration rise of IL-1β associated with cancer", "a fermented milk with suppressing effect of excessive serum concentration rise of TNF-α associated with cancer" or "A fermented milk with suppressing effect of excessive serum concentration rise of CXCL1 associated with cancer".

A Polysaccharide with cancerous cachexia inhibitory effect according to another aspect of the present invention is produced from the above-mentioned *Lactobacillus delbrueckii* subsp. *bulgaricus*.

Incidentally, when the above-mentioned polysaccharide was orally administered to cancerous cachexia model mice, the survival of model mice was improved, and the progression of weight loss was suppressed, and the serum concentration of inflammatory cytokine (IL-1β, TNF-α) and the serum concentration of inflammation-related chemokine (CXCL1) were decreased. That is, the above-mentioned "a polysaccharide with cancerous cachexia inhibitory effect" can be expressed as "a polysaccharide with improving effect of survival of a patient with cancerous cachexia", "a polysaccharide with suppressing effect of weight loss of a patient with cancerous cachexia", "a polysaccharide with lowering effect of serum concentration of inflammatory cytokines", "a polysaccharide with lowering effect of serum concentration of inflammation-related chemokines", "a polysaccharide with suppressing effect of excessive serum concentration rise of IL-1β associated with cancer", "a polysaccharide with suppressing effect of excessive serum concentration rise of TNF-α associated with cancer" or "a polysaccharide with suppressing effect of excessive serum concentration rise of CXCL1 associated with cancer".

A cancerous cachexia inhibitory composition according to further another aspect of the present invention contains the above-mentioned *Lactobacillus delbrueckii* subsp. *bulgaricus* or polysaccharide as an active ingredient. That is, the above-mentioned *Lactobacillus delbrueckii* subsp. *bulgaricus* or polysaccharide is used as a cancerous cachexia inhibitory composition or as a component thereof. The term "composition" as used herein includes preparations such as pharmaceuticals, supplements and food additives; foods and beverages (excluding animals and plants themselves); and food and beverage compositions (including processed foods and beverages), which can be ingested by animals (including humans).

It is noted that the above-mentioned invention can also be expressed as "a method of using *Lactobacillus delbrueckii* subsp. *bulgaricus* or polysaccharide as a cancerous cachexia inhibitor agent", "a *Lactobacillus delbrueckii* subsp. *bulgaricus* or polysaccharide for use as a cancerous cachexia inhibitor agent", "a method of inhibiting cancerous cachexia by orally administering *Lactobacillus delbrueckii* subsp. *bulgaricus* or polysaccharide to a patient with cancerous cachexia". It can also be expressed from another point of view as "use of a *Lactobacillus delbrueckii* subsp. *bulgaricus* or polysaccharide for production of compositions to inhibit cancerous cachexia".

Incidentally, when the above-mentioned *Lactobacillus delbrueckii* subsp. *bulgaricus* or polysaccharide was orally administered to cancerous cachexia model mice, the survival of model mice was improved, and the progression of weight loss was suppressed, and the serum concentration of inflammatory cytokine and inflammation-related chemokine was decreased. That is, the cancerous cachexia inhibitory composition can also be expressed as a survival improving composition of a patient with cancerous cachexia, a weight loss suppressing composition of a patient with cancerous cachexia, a serum concentration lowering composition of an inflammatory cytokine of a patient with cancerous cachexia or a serum concentration lowering composition of an inflammation-related chemokine of a patient with cancerous cachexia.

Effect of the Invention

As a result of intensive studies by the present inventors, it has been revealed that the above-mentioned fermented milk and polysaccharide can inhibit cancerous cachexia. Therefore, when the fermented milk and polysaccharide are administered to a patient with cancerous cachexia, the progress of cancerous cachexia of patient can be suppressed.

BRIEF DESCRIPTION OF THE DRAWINGS

FIG. 1 is a graph showing changes over time in body weight of mice belonging to a control group and mice belonging to a yogurt administration group in Working Example 1. In addition, ○ (open circles) indicates the body weight (g) of mice belonging to yogurt administration group, and ● (closed circles) indicates the body weight (g) of mice belonging to control group.

FIG. 2 is a graph showing changes over time in survival of mice belonging to a control group and mice belonging to a yogurt administration group in Working Example 1.

FIG. 3 is a graph showing changes over time in body weight of mice belonging to a control group and mice belonging to a yoghurt administration group in Working Example 2.

MODE FOR CARRYING OUT THE INVENTION

In the following, the invention will be described in detail by showing of an embodiment of the invention, which is not restricted to the particular embodiments described below.

<Fermented Milk with Cancerous Cachexia Inhibitory Effect>

A fermented milk with cancerous cachexia inhibitory effect according to the embodiment of the present invention contains *Lactobacillus delbrueckii* subsp. *bulgaricus* as an active ingredient.

Preferred *Lactobacillus delbrueckii* subsp. *bulgaricus* include, for example, *Lactobacillus delbrueckii* subsp. *bulgaricus* OLL1073R-1 (accession number: FERM BP-10741). Here, the *Lactobacillus delbrueckii* subsp. *bulgaricus* OLL1073R-1 strain is a lactic acid bacterium internationally deposited under Budapest Treaty under accession number as a FERM BP-10741 to International Patent Organism Depositary in National Institute of Advanced Industrial Science and Technology (Central 6, Tsukuba Center, Higashi 1-1-1, Tsukuba City, Ibaraki Prefecture) on Nov. 29, 2006 (accession date). Note that depositary business of patented microorganisms at International Patent Organism Depositary in National Institute of Advanced Industrial Science and Technology was transferred to National Institute of Technology and Evaluation on Apr. 1, 2012, and Patent Microorganisms Depositary, Biological Resource Center in National Institute of Technology and Evaluation is relocated to the business place of National Institute of Technology and Evaluation at 2-5-8 Kazusakamatari, Kisarazu city, Chiba prefecture, JAPAN on Apr. 1, 2012.

<Extracellular Polysaccharide with Cancerous Cachexia Inhibitory Effect>

An extracellular polysaccharide with cancerous cachexia inhibitory effect according to the embodiment of the present invention is produced in a process of fermenting a raw material containing milk (hereinafter, sometimes referred to as a "milk-containing raw material") by a *Lactobacillus delbrueckii* subsp. *bulgaricus*. That is, the fermented milk with cancerous cachexia inhibitory effect includes the extracellular polysaccharide. In addition, the extracellular polysaccharide may be included in cultures, metabolites and the like obtained by culturing the *Lactobacillus delbrueckii* subsp. *bulgaricus* in a culture medium containing milk. Milk is obtained from a mammal. Here, the type of mammal is not particularly limited, and for example, a primate such as a human, monkey, gorilla, hamadryas baboon, chimpanzee, a domestic animal such as a horse, cow, buffalo, sheep, goat, pig, camel, or deer, a pet animal such as a dog or a cat, or the like can be given. It is preferable that the milk is raw milk, but the milk may be a processed product such as sterile milk, skim milk, total fat powder milk, partial skim milk, skim powder milk, total fat concentrate milk, skim concentrate, cream, butter, butter milk, whey, whey protein concentrate (WPC), whey protein isolate (WPI) or the like.

<Ingestion Body and Ingestion Method of the Above-Mentioned Fermented Milk and Extracellular Polysaccharide>

The fermented milk or the extracellular polysaccharide with cancerous cachexia inhibitory effect according to the embodiment of the present invention exerts its function by being ingested by an animal with a cancerous cachexia condition, in particular, a human. Note that the "human" as used herein may refer to a person of a wide range of ages, from infants to elderly persons, regardless of age and sex. In addition, the fermented milk or extracellular polysaccharide with cancerous cachexia inhibitory effect effectively exerts its function by being ingested by a cancer patient in particular during weight loss or a cancer patient in which weight loss is expected in the future. The "ingestion" as used herein is not limited to an ingestion route as long as it is put into a human body, and can be realized by all known ingestion methods such as, for example, an oral ingestion, a tube ingestion and an enteral ingestion. At this time, there is typically an oral ingestion through the digestive tract and the enteral ingestion, but the oral ingestion is preferable, and the oral ingestion by eating or drinking is more preferable.

The concentration of the extracellular polysaccharide in the fermented milk with cancerous cachexia inhibitory effect according to the embodiment of the present invention is preferably 1 μg/mL or more, more preferably 5 μg/mL or more, still more preferably 10 μg/mL or more, still more preferably 20 μg/mL or more, and particularly preferably 30 μg/mL or more. In this fermented milk, the effect is expected to increase as the content of extracellular polysaccharide increases, but the upper limit is, for example, 0.5 mg/mL.

The mass per unit package of fermented milk according to the embodiment of the present invention is not particularly limited, but from the standpoint of sufficiently obtaining the effect and easy to consume at one time, it is preferable to be within a range of 50 g or more and 500 g or less, more preferable to be within a range of 60 g or more and 200 g or less, more preferable to be within a range of 70 g or more and 150 g or less, and most preferable to be within a range of 80 g or more and 120 g or less. The above-mentioned unit packaging may be not only a unit packaging per bag, box, or container, but also a unit packaging per one time included in them, or a unit packaging per day. Incidentally, it is also possible to package together a plurality of days, for example, a quantity suitable for ingestion for one week, or a package including a plurality of individual packages.

The mass per unit package of extracellular polysaccharide according to the embodiment of the present invention is not particularly limited, but from the standpoint of sufficiently obtaining the effect and being easy to consume at one time, it is preferably within a range of 50 g to 500 g, more preferably within a range of 60 g to 200 g, more preferably within a range of 70 g to 150 g, and most preferably within a range of 80 g to 120 g. The above-mentioned unit packaging may be not only a unit packaging per bag, box, or container, but also a unit packaging per one time included in them, or a unit packaging per day. Incidentally, it is also possible to package together a plurality of days, for example, a quantity suitable for ingestion for one week, or a package including a plurality of individual packages.

It is desirable that the fermented milk or extracellular polysaccharide with cancerous cachexia inhibitory effect according to the embodiment of the present invention is continuously ingested for 1 week or more, preferably 2 weeks or more, more preferably 4 weeks or more. Since the fermented milk or extracellular polysaccharide with cancerous cachexia inhibitory effect according to the embodiment of the present invention can be safely ingested, the ingestion period is not particularly limited and can be permanently continued. The fermented milk or extracellular polysaccharide with cancerous cachexia inhibitory effect may be continuously ingested only for a part of the period, or may be intermittently ingested for an arbitrary period.

<Composition Containing the Above-Mentioned Fermented Milk and Extracellular Polysaccharide>

When the fermented milk or extracellular polysaccharide with cancerous cachexia inhibitory effect according to the embodiment of the present invention is included in a composition (hereinafter, such a composition may be referred to as "a cancerous cachexia inhibitory effect composition"), the content of the fermented milk or extracellular polysaccharide is not particularly limited, but when the cancerous cachexia inhibitory effect composition is a liquid, the fermented milk or extracellular polysaccharide is preferably included so as to contain 1 µg/mL or more of the extracellular polysaccharide, the fermented milk or extracellular polysaccharide is more preferably included so as to contain 5 µg/mL or more of the extracellular polysaccharide, the fermented milk or extracellular polysaccharide is more preferably included so as to contain 10 µg/mL or more of the extracellular polysaccharide, the fermented milk or the extracellular polysaccharide is more preferably included so as to contain 20 µg/mL or more of the extracellular polysaccharide, and the fermented milk or the extracellular polysaccharide is particularly preferably included so as to contain 30 µg/mL or more of the extracellular polysaccharide. It is expected that the effect is enhanced as the content of the extracellular polysaccharide in the cancerous cachexia inhibitory effect composition is increased, but the upper limit is, for example, 0.5 mg/mL.

The mass per unit package of the cancerous cachexia inhibitory effect composition according to the embodiment of the present invention is not particularly limited, but from the standpoint of obtaining sufficient effect and easy to consume once, it is preferable to be within a range of 50 g or more and 500 g or less, more preferable to be within a range of 60 g or more and 200 g or less, more preferable to be within a range of 70 g or more and 150 g or less, and most preferable to be within a range of 80 g or more and 120 g or less. The above-mentioned unit packaging may be not only a unit packaging per bag, box, or container, but also a unit packaging per one time included in them, or a unit packaging per day. Incidentally, it is also possible to package together a plurality of days, for example, a quantity suitable for ingestion for one week, or a package including a plurality of individual packages.

It is desirable that the cancerous cachexia inhibitory effect composition according to the embodiment of the present invention is continuously ingested for 1 week or more, preferably 2 weeks or more, more preferably 4 weeks or more. Since the cancerous cachexia inhibitory effect composition according to the embodiment of the present invention can be safely ingested, the ingestion period is not particularly limited and can be permanently continued. The cancerous cachexia inhibitory effect composition may be continuously ingested only for a part of the time, or may be intermittently ingested for an arbitrary period.

<Form of the Fermented Milk, the Extracellular Polysaccharide or the Cancerous Cachexia Inhibitory Composition>

The fermented milk or extracellular polysaccharide with cancerous cachexia inhibitory effect or the cancerous cachexia inhibitory effect composition according to the embodiment of the present invention can be used as a pharmaceutical, food or drink. The pharmaceutical, food or drink is useful in that it has an effect of inhibiting cancerous cachexia. When the fermented milk or extracellular polysaccharide with cancerous cachexia inhibitory effect or the cancerous cachexia inhibitory effect composition according to the embodiment of the present invention is used as a pharmaceutical, food or drink, the extracellular polysaccharide obtained from a single *Lactobacillus delbrueckii* subsp. *bulgaricus* may be used, or the extracellular polysaccharide obtained from two or more types of *Lactobacillus delbrueckii* subsp. *bulgaricus* may be used in combination.

When the fermented milk or extracellular polysaccharide with cancerous cachexia inhibitory effect or the cancerous cachexia inhibitory effect composition according to the embodiment of the present invention is used as a pharmaceutical, food or drink, the state thereof is not particularly limited, and may be in a state of paste, spray dried product, lyophilized product, vacuum dried product, drum dried product, liquid product dispersed in a medium, diluted product diluted with a diluent, crushed product obtained by crushing the dried product with a mill, or the like.

Further, the fermented milk or extracellular polysaccharide with cancerous cachexia inhibitory effect or the cancerous cachexia inhibitory effect composition according to the embodiment of the present invention may be a food with health claims or a food for a sick person (such as a cancerous cachexia inhibitory effect food). The system for food with health claims is established for not only ordinary foods but also foods in the form of tablets, capsules and the like based on domestic and overseas trends and consistency with the conventional system for food for specified health use. The system stipulates three types of food for specified health use (individually permitted type), food with nutrient function claims (standard type) and food with functional claims. By administering the fermented milk or extracellular polysaccharide with cancerous cachexia inhibitory effect or the cancerous cachexia inhibitory effect composition according to the embodiment of the present invention to an animal such as a human as a special purpose food such as food for specified health use or a nutritionally functional food, the cancerous cachexia can be suppressed.

To the fermented milk or extracellular polysaccharide with cancerous cachexia inhibitory effect or the cancerous cachexia inhibitory effect composition according to the embodiment of the present invention, it is preferable to label an description of the use, the efficacy, the function, the type of the active ingredient, the type of functional ingredient, the ingestion method, and the like. "Labeling" as used herein should be appropriate labeling for drugs, quasi-drugs, food with health claims, food for specified health use, food with functional claims, general foods, dietary supplement, healthy food and supplements, respectively. Also, "labeling" herein includes all labeling for informing the consumer of the above description. This labeling may be any labeling capable of recalling or analogizing the above-mentioned labeling content, and may include any labeling regardless of the purpose of labeling, the content of labeling, the object to be labeled, the medium or the like. For example, the description may be labeled on a package or container of a product, the product may be displayed or distributed labeling the above-mentioned description on an advertisement, price list or transaction document related to the product, or an information containing the description may be provided by an electromagnetic (Internet or the like) method.

When the product obtained by packaging the fermented milk or extracellular polysaccharide with cancerous cachexia inhibitory effect or the cancerous cachexia inhibitory effect composition according to the embodiment of the present invention is, for example, a food or drink, it is preferable that, for example, a labeling of "inhibition of cancerous cachexia" or a labeling of "inhibition of progression of cancerous cachexia symptoms" is attached to the food or drink.

Note that the words used for performing the above-mentioned labeling are not limited to the above-mentioned examples, and may be words having the same meaning as the above-mentioned examples. As such words, for example, various words such as "inhibit cancerous cachexia," "help inhibit the onset of cancerous cachexia," or "help inhibit the progression of cancerous cachexia" may be permitted to users.

When the extracellular polysaccharide with cancerous cachexia inhibitory effect or the cancerous cachexia inhibitory effect composition according to the embodiment of the present invention is used as a food or drink, the type of food or drink is not particularly limited. The food and drink may be, for example, milk, processed milk, soft drink, cheese, other dairy products, bread, biscuits, crackers, pizza crusts, formula milk, liquid foods, food for a sick person, infant formula food, pregnant and nursing formula food, nutritional foods and the like. In the manufacture of such foods and drinks, it is possible to utilize a manufacturing method in an ordinary food composition, such as using the extracellular polysaccharide with cancerous cachexia inhibitory effect or the cancerous cachexia inhibitory effect composition according to the embodiment of the present invention as it is, or mixing them with other foods and/or drinks or food components. The shape of food or drink is not particularly limited, and may be any shape as long as it is a normally used food or drink. For example, it may be in any form including, but not limited to, solid (including powder, granular), paste, liquid, suspension and the like. At this time, a milk beverage, a soft drink, a jelly beverage, a tablet, and a powdered food are more preferable.

The fermented milk or extracellular polysaccharide with cancerous cachexia inhibitory effect or the cancerous cachexia inhibitory effect composition according to the embodiment of the present invention can be added without any problem as long as it is a component contained in a normal food such as water, protein, sugar, lipid, vitamin, mineral, organic acid, organic base, fruit juice, flavor, functional component, food additives or the like. In the production of the above food or beverage, protein or protein-containing raw materials commonly used in food production, such as, for example, animal and plant proteins such as soy protein, milk protein, chicken egg protein, and meat protein, and hydrolysates thereof, can be used as a protein source. Examples of sources of the sugar include processed starch (dextrin, soluble starch, British starch, oxidized starch, starch esters, starch ethers and the like), dietary fiber and the like. Examples of the lipid source include animal oils and fats such as lard, fish oils and the like, fractionated oils thereof; hydrogenated oils, ester exchange oils and the like; vegetable oil such as palm oil, safflower oil, corn oil, rapeseed oil, coconut oil, fractionated oils thereof, hydrogenated oils, ester exchange oils and the like. Examples of the vitamin include vitamin A, carotenes, vitamin B group, vitamin C, vitamin D group, vitamin E, vitamin K group, vitamin P, vitamin Q, niacin, nicotinic acid, pantothenic acid, biotin, inositol, choline, folic acid and the like, and examples of the mineral include calcium, potassium, magnesium, sodium, copper, iron, manganese, zinc, selenium and the like. Examples of the organic acid include, for example, malic acid, citric acid, lactic acid, tartaric acid and the like. Functional component includes, for example, oligosaccharide, glucosamine, collagen, ceramide, royal jelly, polyphenol and the like. Food additives include, for example, emulsifier, stabilizer, thickener, gelling agent, sweetener, acidulate, preservative, antioxidant, pH adjuster, colorant, flavor and the like. Various milk-derived components such as butter, milk mineral, cream, whey, non-protein nitrogen, sialic acid, phospholipid, lactose and the like are examples of components which can be suitably used for the production of the food and drink according to the embodiment of the present invention. Further, any components with cancerous cachexia inhibitory effect may be added to the fermented milk or extracellular polysaccharide with cancerous cachexia inhibitory effect or the cancerous cachexia inhibitory effect composition according to the embodiment of the present invention.

Two or more of these components can be used in combination. The above-mentioned raw material may be any of a natural product, a natural product processed product, a synthetic product, and/or a food containing many of them.

Incidentally, the present inventors have confirmed that the fermented milk or extracellular polysaccharide with the above-mentioned cancerous cachexia inhibitory effect or the cancerous cachexia inhibitory effect composition improves the survival of a cancer patient, suppresses the weight loss of a cancer patient, and lowers the serum concentration of inflammatory cytokine and inflammation-related chemokine of a cancer patient. Therefore, the fermented milk or extracellular polysaccharide with cancerous cachexia inhibitory effect or the cancerous cachexia inhibitory effect composition according to the embodiment of the present invention can be said to be a fermented milk or extracellular polysaccharide with suppressing effect of weight loss of a cancer patient or composition for suppressing weight loss of a cancer patient, a fermented milk or extracellular polysaccharide with lowering effect of serum concentration of inflammatory cytokine of a cancer patient, composition for lowering serum concentration of inflammatory cytokine of a cancer patient, fermented milk or extracellular polysaccharide with lowering effect of serum concentration of inflammation-related chemokine of a cancer patient, composition for lowering serum concentration of inflammation-related chemokine of a cancer patient. That is, when the product obtained by packaging the fermented milk or extracellular polysaccharide with cancerous cachexia inhibitory effect or the cancerous cachexia inhibitory effect composition according to the embodiment of the present invention is, for example, a food or drink, for example, a label of "suppressing weight loss of a cancer patient", "lowering a serum concentration of an inflammatory cytokine of a cancer patient", "lowering a serum concentration of an inflammation-related chemokine of a cancer patient" and the like may be attached to the food or drink.

The present inventors have also confirmed that serum concentrations of IL-1β and TNF-α are lowered as specific effects of the fermented milk or extracellular polysaccharide with lowering effect of serum concentration of inflammatory cytokine of the above-mentioned cancer patient or composition for lowering serum concentration of inflammatory cytokine of the cancer patient. Therefore, the fermented milk or extracellular polysaccharide with cancerous cachexia inhibitory effect or the cancerous cachexia inhibitory effect composition according to the embodiment of the present invention can be said to be a fermented milk or extracellular polysaccharide with lowering effect of serum concentration of IL-1β, a composition for lowering IL-1β serum concentration of a cancer patient, a fermented milk or extracellular polysaccharide with lowering effect of serum concentration of TNF-α or a composition for lowering TNF-α serum concentration of a cancer patient.

In addition, the present inventors have confirmed that a serum concentration of CXCL1 is lowered as a specific effect of the fermented milk or the extracellular polysaccharide with lowering effect of serum concentration of inflammation-related chemokine e of the above-mentioned cancer patient or composition for lowering serum concentration of inflammation-related chemokine of the cancer patient. Therefore, the fermented milk or extracellular polysaccharide with suppressing effect of the cancerous cachexia or the composition for suppressing the cancerous cachexia according to the embodiment of the present invention can be said to be the fermented milk or extracellular polysaccharide with lowering effect of serum concentration of CXCL1 or composition for lowering serum concentration of CXCL1 of the cancer patient.

The extracellular polysaccharide or *Lactobacillus delbrueckii* subsp. *bulgaricus* may be a cancerous cachexia inhibitory drug, a weight loss suppressive drug for cancer patient, an inflammatory cytokine serum concentration lowering drug for a cancer patient, an IL-1β serum concentration lowering drug for a cancer patient, a TNF-α serum concentration lowering drug for a cancer patient or a CXCL1 serum concentration lowering drug for a cancer patient. In the manufacture of such a pharmaceutical product, the extracellular polysaccharide or *Lactobacillus delbrueckii* subsp. *bulgaricus* can be used as a crushed or uncrushed treatment. The extracellular polysaccharide used in this case may be an extracellular polysaccharide obtained from a single *Lactobacillus delbrueckii* subsp. *bulgaricus* or a combination of extracellular polysaccharide obtained from two or more types of *Lactobacillus delbrueckii* subsp. *bulgaricus*. In addition, the *Lactobacillus delbrueckii* subsp. *bulgaricus* used in this case may be a single *Lactobacillus delbrueckii* subsp. *bulgaricus* or a combination of two or more *Lactobacillus delbrueckii* subsp. *bulgaricus*.

The content of extracellular polysaccharide in the above-mentioned pharmaceutical product can be arbitrarily determined according to its purpose and use. An example of the content is 1 μg/mL, but is not limited to this in the embodiment of the present invention.

The dosage of the above-mentioned pharmaceutical product containing the extracellular polysaccharide as an active ingredient can be appropriately set in consideration of various factors such as a route of administration, age, body weight, and symptoms of a subject animal including humans. Examples of suitable dosages include, but are not limited to, 0.01 mg to 1000 mg/kg/day of active ingredient. Since there is no safety problem with the extracellular polysaccharide which is the active ingredient, a larger amount than the above range may be used.

The dosage form of the above-mentioned pharmaceutical product is preferably a dosage form capable of being orally dosed because it causes the extracellular polysaccharide or *Lactobacillus delbrueckii* subsp. *bulgaricus* to reach the intestine. Examples of preferred dosage forms of the pharmaceutical product according to the embodiments of the present invention include, for example, tablet, pill, coated tablet, capsule, granule, powder, solution, suspension, emulsion, syrup, lozenge and the like. These various formulations may be formulated by mixing the extracellular polysaccharide or *Lactobacillus delbrueckii* subsp. *bulgaricus*, which is a main agent according to conventional methods, with auxiliaries which may be commonly used in the pharmaceutical formulation art, such as excipient, binder, disintegrant, lubricant, stabilizer, coloring agent, flavoring agent, dissolving aid, suspensions, surfactant, coating and the like.

In addition, when using the extracellular polysaccharide or *Lactobacillus delbrueckii* subsp. *bulgaricus* as the pharmaceutical product, for example, in the case of oral administration, the extracellular polysaccharide or *Lactobacillus delbrueckii* subsp. *bulgaricus* can be taken as they are, but they can be, for example, tablet, granule, powder, capsule, or powder according to the general preparation method of the pharmaceutical product.

The content of extracellular polysaccharide or *Lactobacillus delbrueckii* subsp. *bulgaricus* in the above pharmaceutical products can be appropriately determined according to the form, use, age, gender, type and degree of progress of cancer, degree of weight loss and other conditions of a patient.

The above-mentioned pharmaceutical product is preferably administered orally. By administering this pharmaceutical product, cancerous cachexia can be inhibited or the weight loss of cancer patient can be suppressed. Thus, the pharmaceutical product is useful for suppression or alleviation of various symptoms caused by cancerous cachexia. In addition, as long as the inhibiting effect of cancerous cachexia according to the embodiment of the present invention is not impaired, this pharmaceutical product containing the extracellular polysaccharide or *Lactobacillus delbrueckii* subsp. *bulgaricus* as an active ingredient may be used in combination with another pharmaceutical product.

WORKING EXAMPLES

The following working examples are provided to explain the invention in more detail, but are not intended to limit the invention to the following working examples.

Preparation Example 1

A desired yoghurt was prepared by adding *Lactobacillus delbrueckii* subsp. *bulgaricus* OLL1073R-1 (accession number: FERM BP-10741) and *Streptococcus thermophiles* as a lactic acid bacterium starter into skim dry milk medium and fermenting the skim dry milk medium at 43° C. for 2.5 h.

Preparation Example 2

A desired yoghurt was prepared by adding *Lactobacillus delbrueckii* subsp. *bulgaricus* OLL1073R-1 (accession number: FERM BP-10741) and *Streptococcus thermophiles* as a lactic acid bacterium starter into mixtures containing raw milk, skim milk powder, creams, sugars and *stevia* and fermenting the skim milk powder medium at 43° C. for 3.5 h.

Working Example 1

First, a total of 15 of BALB/c mice, males, 7 weeks of age (sold by Charles River, Japan) were divided into a control group (7 mice) and a yogurt administration group (8 mice). Then, colon26 single cell suspension (in PBS) as a mouse colon cancer-derived cells was prepared and its colon26 single cell suspension was implanted into the left ventral subcutaneous of each mouse (total 15 mice) using a 26G injection needle (manufactured by Terumo Corporation) at $6.0\times10^5$ cells/200 µL. Then, the mice in the control group were given 400 µL of 10% skim milk powder medium by compulsory oral administration, and the mice in the yogurt administration group were given 400 µL of yogurt prepared in the preparation Example 1 by compulsory oral administration. The compulsory oral administration to the mice in the yogurt administration group was performed once daily from the day of transplantation of colon26 cells into the same mice to the day before dissection of the same mice. Weights of the mice were measured three times a week from the day elapsed 21 days from the day of colon26 cell transplantation, and the mice were euthanized as humane endpoints when cachexia progressed severely and the body weight dropped below 20 g. Follow-up of the mice was continued until the day elapsed 35 days from the day of colon26 cell-transplantation, and all surviving mice were euthanized at the day elapsed 35 days.

The body weights of mice belonging to both groups at the day elapsed 21 days from the day of colon26 cell transplantation were compared by Student's t-test and showed that mice belonging to the yogurt administration group tended to be heavier than those belonging to the control group (p=0.056) (see FIG. 1). In addition, when the survival of mice from the start day of the experiment to the day elapsed 35 days was compared by the Kaplan-Meier log-rank test, the survival of mice belonging to the yoghurt administration group was significantly improved (p=0.045) (see FIG. 2).

Working Example 2

First, a total of 12 of BALB/c mice, males, 5 weeks of age (sold by Charles River, Japan) were divided into a control group (6 mice) and a yogurt administration group (6 mice). Next, 400 µL of distilled water was compulsorily orally administrated per each mouse belonging to the control group, and 400 µL of yogurt prepared in the preparation Example 2 was compulsorily administrated per each mouse belonging to the yogurt administration group. Compulsory oral administration was performed to mice in each group once daily until the day before dissection. Then, in the day elapsed 13 days from the start of the compulsory oral administration, colon26 single cell suspension (in PBS) as a mouse colon cancer-derived cells was prepared, and the colon26 single cell suspension was transplanted into the right axillary subcutaneous of each mouse (total 12 mice) using a 26G injection needle (manufactured by Terumo Corporation) at $8.0\times10^5$ cells/200 µL. In addition, from the day of transplantation of colon26 cells to the day of dissection of mice, a metabolic improver, metformin (manufactured by Wako Pure Chemical Industries, Ltd.) was administered in free drinking water (5 mg/mL) to all mice. Since metformin is known to improve cancerous cachexia (improvement with nutritional and metabolic effects) through improving sugar and protein metabolisms, it was conducted to show that the cancerous cachexia inhibitory effect caused by *Lactobacillus delbrueckii* subsp. *bulgaricus* OLL1073R-1 is due to immunological rather than nutritional and metabolic effects. Body weight measurements of mice were started twice weekly from the day elapsed 4 days from the day of transplantation of colon26 cells. All mice were euthanized at the day elapsed 14 days from the day of colon26 cell-transplantation and blood was collected from each mouse. Thereafter, Bio-Plex Pro mouse cytokine GI 23-Plex panel, which is an assay kit for measuring the cytokine (manufactured by BIO-RAD) was used to measure the concentration of 23 items of serum cytokine of the blood of each mouse.

When the body weights of the mice belonging to both groups at the day elapsed 14 days from the day of colon26 cell transplantation were compared by Student's t-test, the mice belonging to the yogurt administration group tended to be heavier than the mice belonging to the control group (p=0.061) (see FIG. 3). When twenty-three serum cytokine concentrations in the blood of mice belonging to both groups were compared, the concentrations of IL-1β and TNFα, representative inflammatory cytokines, and CXCL1, an inflammation-related chemokine that recruits neutrophils to sites of inflammation, were significantly lower in mice belonging to the yogurt administration group than in mice belonging to the control group (see Table 1).

TABLE 1

| | | IL-1β | TNF-α | CXCL1 |
|---|---|---|---|---|
| Control group | Av. | 17.71 pg/ml | 155.07 pg/ml | 392.18 pg/ml |
| | Std. dev. | 3.76 pg/ml | 17.11 pg/ml | 139.14 pg/ml |
| yoghurt administration group | Av. | 12.76 pg/ml | 116.69 pg/ml | 144.85 pg/ml |
| | Std. dev. | 3.12 pg/ml | 25.24 pg/ml | 48.32 pg/ml |
| p value (t-test) | | 0.032 | 0.012 | 0.006 |

INDUSTRIAL APPLICABILITY

A fermented milk and polysaccharide with cancerous cachexia inhibitory effect according to the present invention can inhibit cancerous cachexia, and is expected to contribute to prolongation of the life of cancer patient and the like.

[Accession No.]
FERM BP-10741

The invention claimed is:

1. A method for inhibiting cancerous cachexia in an individual comprising
    administering a fermented milk comprising *Lactobacillus delbrueckii* subsp. *bulgaricus* to an individual in need thereof,
    wherein the *Lactobacillus delbrueckii* subsp. *bulgaricus* produces a polysaccharide, and
    wherein the fermented milk is administered in a quantity such that a dosage of 0.01 mg/kg/day to 1000 mg/kg/day of the polysaccharide is administered to the individual in need thereof.

2. The method according to claim 1, the *Lactobacillus delbrueckii* subsp. *bulgaricus* is *Lactobacillus delbrueckii* subsp. *bulgaricus* OLL1073R-1 (accession number: FERM BP-10741).

3. A method for inhibiting cancerous cachexia in an individual comprising administering a polysaccharide produced from *Lactobacillus delbrueckii* subsp. *bulgaricus* to an individual in need thereof, wherein the polysaccharide is administered in a dosage of 0.01 mg/kg/day to 1000 mg/kg/day.

4. The method according to claim 3, the *Lactobacillus delbrueckii* subsp. *bulgaricus* is *Lactobacillus delbrueckii* subsp. *bulgaricus* OLL1073R-1 (accession number: FERM BP-10741).

* * * * *